(12) United States Patent
Botros

(10) Patent No.: US 8,880,182 B2
(45) Date of Patent: Nov. 4, 2014

(54) FITTING A COCHLEAR IMPLANT

(75) Inventor: Andrew Botros, Maroubra (AU)

(73) Assignee: Cochlear Limited, Macquarie University, NSW (AU)

( * ) Notice: Subject to any disclaimer, the term of this patent is extended or adjusted under 35 U.S.C. 154(b) by 608 days.

(21) Appl. No.: 12/809,579

(22) PCT Filed: Dec. 17, 2008

(86) PCT No.: PCT/AU2008/001865
§ 371 (c)(1),
(2), (4) Date: Jun. 18, 2010

(87) PCT Pub. No.: WO2009/076721
PCT Pub. Date: Jun. 25, 2009

(65) Prior Publication Data
US 2010/0268302 A1    Oct. 21, 2010

(30) Foreign Application Priority Data
Dec. 18, 2007    (AU) ................ 2007906933

(51) Int. Cl.
*A61N 1/36* (2006.01)
*A61N 1/372* (2006.01)

(52) U.S. Cl.
CPC ......... *A61N 1/36032* (2013.01); *A61N 1/37252* (2013.01)
USPC .......................................................... 607/57

(58) Field of Classification Search
CPC . A61N 1/36032; A61N 1/37252; A61N 1/36; A61N 1/36128; A61N 1/36146; A61N 1/3615; A61N 1/36189; A61N 1/36192; A61N 1/37
USPC .................. 607/55–57, 60, 62, 137
See application file for complete search history.

(56) References Cited

U.S. PATENT DOCUMENTS

| 4,532,930 A | 8/1985 | Crosby et al. |
| 5,724,433 A | 3/1998 | Engebretson et al. |
| 5,758,651 A | 6/1998 | Nygard et al. |
| 6,190,306 B1 | 2/2001 | Kennedy |
| 6,205,360 B1 | 3/2001 | Carter et al. |
| 6,537,200 B2 | 3/2003 | Leysieffer et al. |

(Continued)

FOREIGN PATENT DOCUMENTS

| EP | 2071873 | 6/2009 |
| JP | 11-513539 | 11/1999 |
| WO | 2005/122887 A2 | 12/2005 |
| WO | 2008031169 A1 | 3/2008 |

OTHER PUBLICATIONS

International Search Report, PCT/AU2008/001865, mailed Mar. 12, 2009.
Written Opinion, PCT/AU2008/001865, mailed Mar. 12, 2009.

(Continued)

*Primary Examiner* — Carl H Layno
*Assistant Examiner* — Jessica Anthony
(74) *Attorney, Agent, or Firm* — K&L Gates LLP

(57) ABSTRACT

A computer-implemented method for fitting a medical implant to a recipient, the medical implant being operative to stimulate a physiological system of the recipient over a plurality of stimulation channels. The method includes: determining, based on measurements, an initial stimulation profile for the plurality of stimulation channels; determining a representative stimulus level of the initial stimulation profile; determining a fitting stimulation profile by modifying the shape a shape of the initial stimulation based on the representative stimulus level profile; and configuring the medical implant according to the fitting stimulation profile.

14 Claims, 10 Drawing Sheets

(56) References Cited

U.S. PATENT DOCUMENTS

| | | |
|---|---|---|
| 6,565,503 B2 | 5/2003 | Leysieffer et al. |
| 6,575,894 B2 | 6/2003 | Leysieffer et al. |
| 6,697,674 B2 | 2/2004 | Leysieffer |
| 6,915,166 B1 | 7/2005 | Stecker et al. |
| 6,951,166 B1 | 10/2005 | Sickels |
| 7,010,136 B1 | 3/2006 | Roberts et al. |
| 7,076,308 B1 | 7/2006 | Overstreet et al. |
| 7,117,038 B1 | 10/2006 | Overstreet |
| 2002/0176584 A1 | 11/2002 | Kates |
| 2004/0167586 A1 | 8/2004 | Overstreet |
| 2006/0235332 A1 | 10/2006 | Smoorenburg |
| 2006/0287690 A1 | 12/2006 | Bouchataoui et al. |
| 2007/0255344 A1 | 11/2007 | Van Dijk |
| 2012/0109006 A1 | 5/2012 | James et al. |

OTHER PUBLICATIONS

European Search Report and Search Opinion for European Application No. 08861452.4 mailed Nov. 30, 2011.

Japanese Office Action for Japanese Application No. 2010-538276 mailed Apr. 23, 2013 along with an English translation.

International Search Report and Written Opinion for International Application No. PCT/IB2011/054808 mailed Apr. 27, 2012 (8 pages).

FITTING A COCHLEAR IMPLANT

CROSS-REFERENCE TO RELATED APPLICATIONS

The present application is a National Stage Application of International Application No. PCT/AU2008/001865, filed Dec. 17, 2008 entitled "Method and System For Fitting a Cochlear Implant", which claims priority from Australian Provisional Patent Application No. 2007906933 entitled "Method and System for Fitting a Cochlear Implant", filed 18 Dec. 2007, which is hereby incorporated by reference herein.

BACKGROUND

1. Field of the Invention

The present invention relates generally to the configuration of a medical implant that stimulates a physiological system of a recipient, and more particularly, to fitting of a cochlear implant.

2. Related Art

There are many medical implants that deliver electrical stimulation to a recipient for a variety of therapeutic benefits. For example, cochlear implants, such as those manufactured by Cochlear Limited, Sydney, Australia, have been developed to provide persons suffering from sensorineural hearing loss with the ability to perceive sound. The hair cells of the cochlea of a normal healthy ear convert acoustic signals into nerve impulses. People who are profoundly deaf due to the absence or destruction of cochlea hair cells are unable to derive suitable benefit from conventional hearing aid systems. Cochlear implants have been developed to provide such persons with the ability to perceive sound.

Cochlear implants typically comprise external and implanted or internal components that cooperate with each other to provide sound sensations to the recipient. The external component traditionally includes a microphone that detects sounds, such as speech and environmental sounds, a speech processor that selects and converts certain detected sounds, particularly speech, into a coded signal, a power source such as a battery, and an external transmitter antenna.

The coded signal output by the speech processor is transmitted transcutaneously to an implanted receiver/stimulator unit. This transcutaneous transmission occurs via the external transmitter antenna which is positioned to communicate with an implanted receiver antenna disposed within the receiver/stimulator unit. This communication transmits the coded sound signal while also providing power to the implanted receiver/stimulator unit.

The implanted receiver/stimulator unit also includes a stimulator that processes the coded signal and outputs an electrical stimulation signal to an intra-cochlear electrode assembly. The electrode assembly typically has a plurality of electrodes that apply electrical stimulation to the auditory nerve to produce a hearing sensation corresponding to the original detected sound.

Following surgical implantation of the internal components (including the receiver/stimulator unit and intra-cochlear electrode assembly), the cochlear implant system must be configured (or fitted) for each individual recipient. This configuration procedure is normally carried out by an audiologist several weeks after implantation.

An important aspect of this configuration procedure is the collection and determination of a number of recipient-specific input configuration variables that are required for normal operation of the cochlear implant system. Two of the input configuration variables that require determination include the threshold level of electrical stimulation (known as a T level), and the maximum comfort level of electrical stimulation (known as a C level) for each electrode stimulation channel. Together, the T and C levels define a "dynamic range" of electrical stimulation for each electrode channel.

The T level is defined as the level at which the recipient first identifies sound sensation, and is the lowest level at which the recipient hears the stimulus. The C level sets the maximum allowable stimulation level for each electrode and is defined as the maximum stimulation level that does not produce an uncomfortable loudness sensation for the recipient.

Conventionally, T and C levels are manually determined by a clinician working together with the recipient. For each stimulation channel of the implant, the clinician applies stimulation pulses and then receives an indication from the recipient as to the level and comfort of the resulting sound.

Referring to FIG. 2, there is shown graphically the settings 200 for the T and C levels for each electrode 210 in a 22 electrode system as determined by a clinical fitting procedure. The set of T levels and C levels across the electrode array constitute a T level profile 220 and a C level profile 230, respectively. If a T level is set too low, then stimuli are applied which cannot be perceived. If the C level is set too high, then the recipient may be overstimulated, leading to pain and possible injury to the recipient.

This post-operative configuration or fitting process can be extremely time consuming. In locations where there is a lack of adequate audiological infrastructure and/or trained clinicians, the cochlear implant may not be optimally fitted for some recipients. Additionally, since this post-operative configuration process relies on subjective measurements, children, pre-lingually deaf or congenitally deaf recipients are often unable to provide an accurate impression of the hearing sensation resulting from the stimulation test pulses. This further complicates the fitting process, potentially resulting in a cochlear implant that is not optimally fitted.

Referring now to FIG. 3, in an attempt to improve the efficiency of the fitting process one approach has been to base the shape of one type of profile on the shape of another type of profile. An example of this approach is depicted in settings 300, wherein the shape of the C level profile 330 (i.e. the electrode to electrode variation in level) is first matched to the shape of the corresponding T level profile 320. Following this matching process, C level profile 330 is then shifted to achieve comfortable loudness for the recipient.

Accordingly, the C levels 330 of the electrodes 310 are based only on the shape of T level profile 320 and a shift measure $\Delta S$. Thus the relative differences in stimulus level between adjacent electrodes for the C level profile 330 are maintained in accordance with the T level profile 320. Only the overall mean stimulus level then needs to be manipulated by changing $\Delta S$ to achieve comfortable loudness.

In another approach, objective measures of the auditory system are employed to simplify the task of configuring the cochlear implant. Cochlear implant objective measures include those physiological signals that are related to the auditory system, such as the electrically evoked auditory nerve action potential (ECAP), the auditory brain stem response (EABR) or the stapedius reflex (ESR). These physical characteristics of the auditory system are described in detail in Cullington H. E., Cochlear Implants: Objective Measures, London, Whurr Publishers, 2003.

These and other physical characteristics can be measured by employing a cochlear implant system such as the Cochlear™ Nucleus™ system employing Neural Response Telemetry (NRT) where the minimum stimulus level required to evoke a detectable response can be determined on each electrode. The telemetry mode enables a telemetry facility within the cochlear implant to measure various physical characteristics of the recipient's physiological system.

In this telemetry mode, the implanted electrode array is used to provide test stimuli and to then measure a neural response of the recipient's physiological system. The test stimuli are delivered by means of a number of "stimulation channels." For example, the delivery of a stimulation current between two particular electrodes of the electrode array may be defined as stimulation via channel 1. Similarly, other combinations of electrodes involved in stimulation delivery will also define other stimulation channels. An exemplary telemetering arrangement is described in U.S. Pat. No. 5,758,651. The profile of these objectively measured physical thresholds constitutes another type of profile that may be replicated.

Referring now to FIG. 4, there is shown graphically the settings 400 for a T level profile 420 and C level profile 430 that have been matched to an objective threshold profile 440. In this example, an ECAP threshold has been measured for each electrode 410, resulting in ECAP threshold profile 440. The T level profile 420 and C level profile 430 are then set at constant offsets $\Delta S_1$ and $\Delta S_2$ from ECAP threshold profile 440. These offsets are determined by the clinical measurement on a single channel, typically a mid-frequency channel, and then applied accordingly across all channels.

However, while this approach has the effect of reducing the time required for the clinical fitting of a cochlear implant, it clearly suffers from a number of disadvantages. The primary disadvantage is the assumption that the shape of the profile determined at a first level (typically an objectively measured or clinically determined threshold level) will relate to the shape of the profile at a second level at a different overall mean or stimulus level. This will not take into account variations in the auditory system that depend on stimulus level.

SUMMARY

In one aspect of the present invention, a method for fitting a medical implant to a recipient, the medical implant operative to stimulate a physiological system of the recipient over a plurality of stimulation channels is disclosed. The method comprising: determining an initial stimulation profile for the plurality of stimulation channels; and determining a fitting stimulation profile by modifying the shape of the initial stimulation profile.

In a second aspect of the present invention, a method for fitting a stimulating hearing prosthesis operative to stimulate a portion of the auditory system of the recipient over a plurality of stimulation channels is disclosed. The method comprising:determining an initial stimulation profile for the plurality of stimulation channels; and determining a fitting stimulation profile by shifting the initial stimulation profile to a desired stimulation level, and flattening or broadening the shape of the initial stimulation profile based on whether the mean stimulation level of the fitting stimulation profile is greater or lesser than the mean stimulation level of the initial stimulation profile.

BRIEF DESCRIPTION OF THE DRAWINGS

Illustrative embodiments of the present invention are described herein with reference to the accompanying drawings, in which.

DETAILED DESCRIPTION

Figure 1:
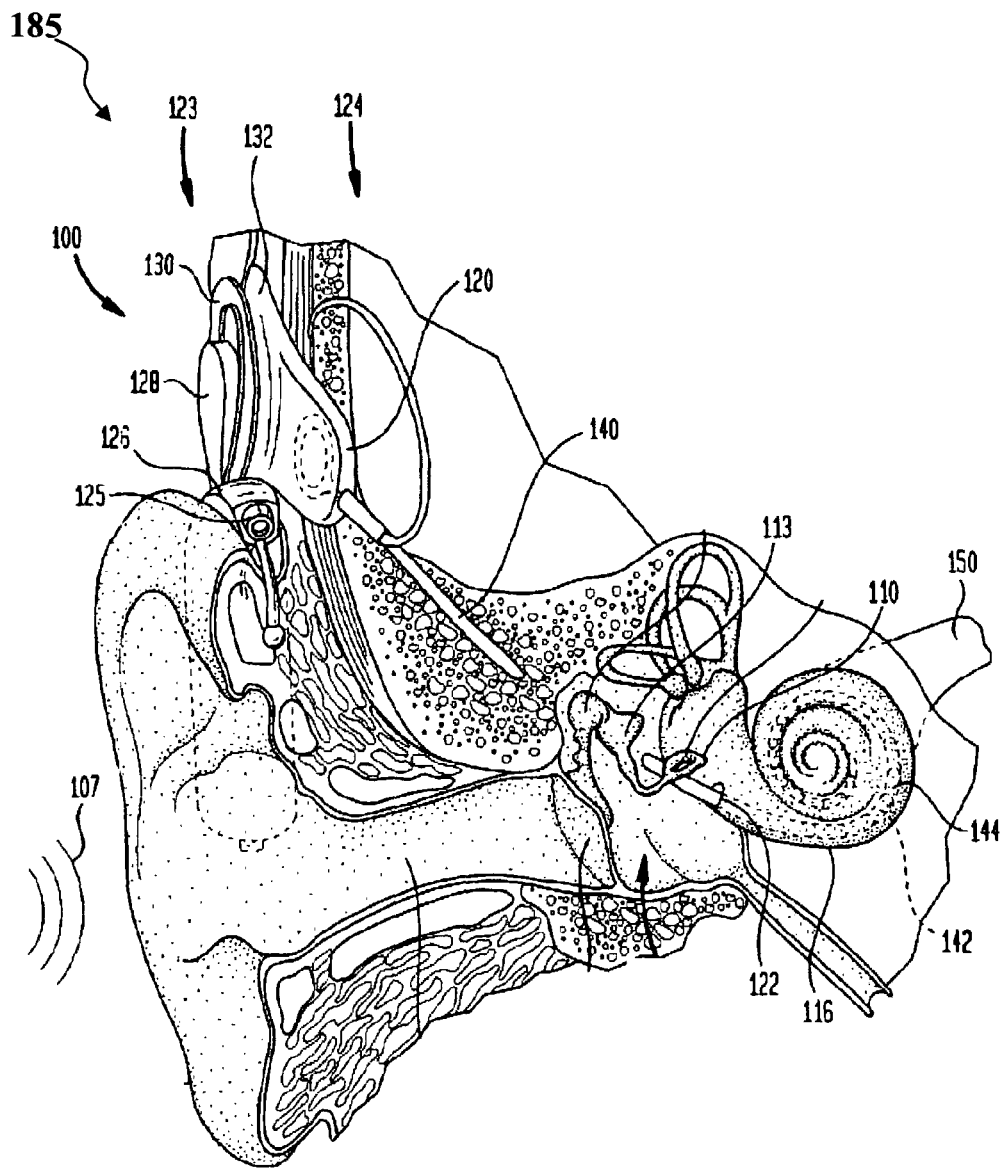
FIG. 1 is an exemplary cochlear implant which may be advantageously fitted with embodiments of the present invention.
Figure 2:
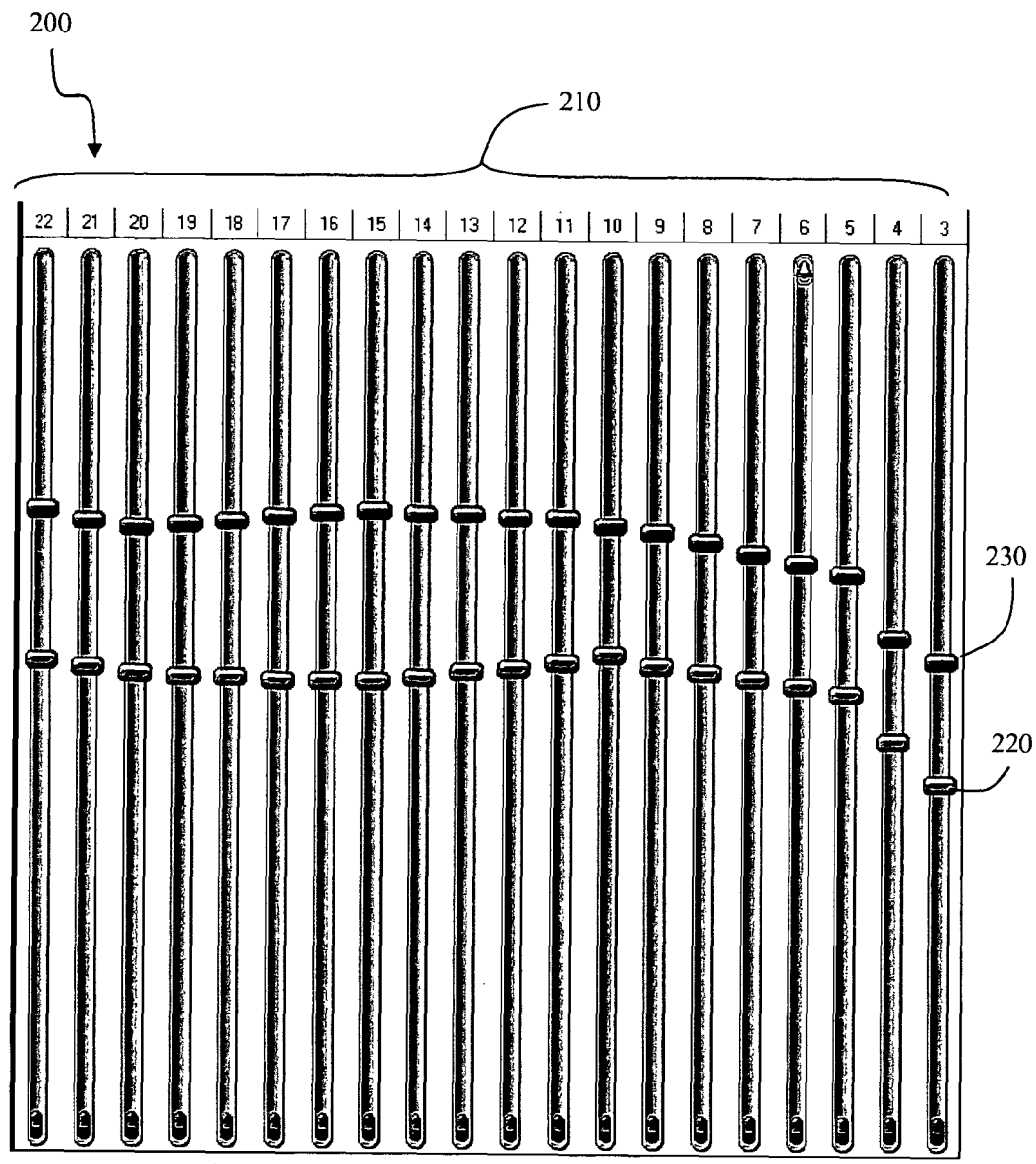
FIG. 2 is a graph of the T levels and C levels as a function of electrode number depicting the T and C level profiles as determined by direct measurement from a cochlear implant recipient.
Figure 3:
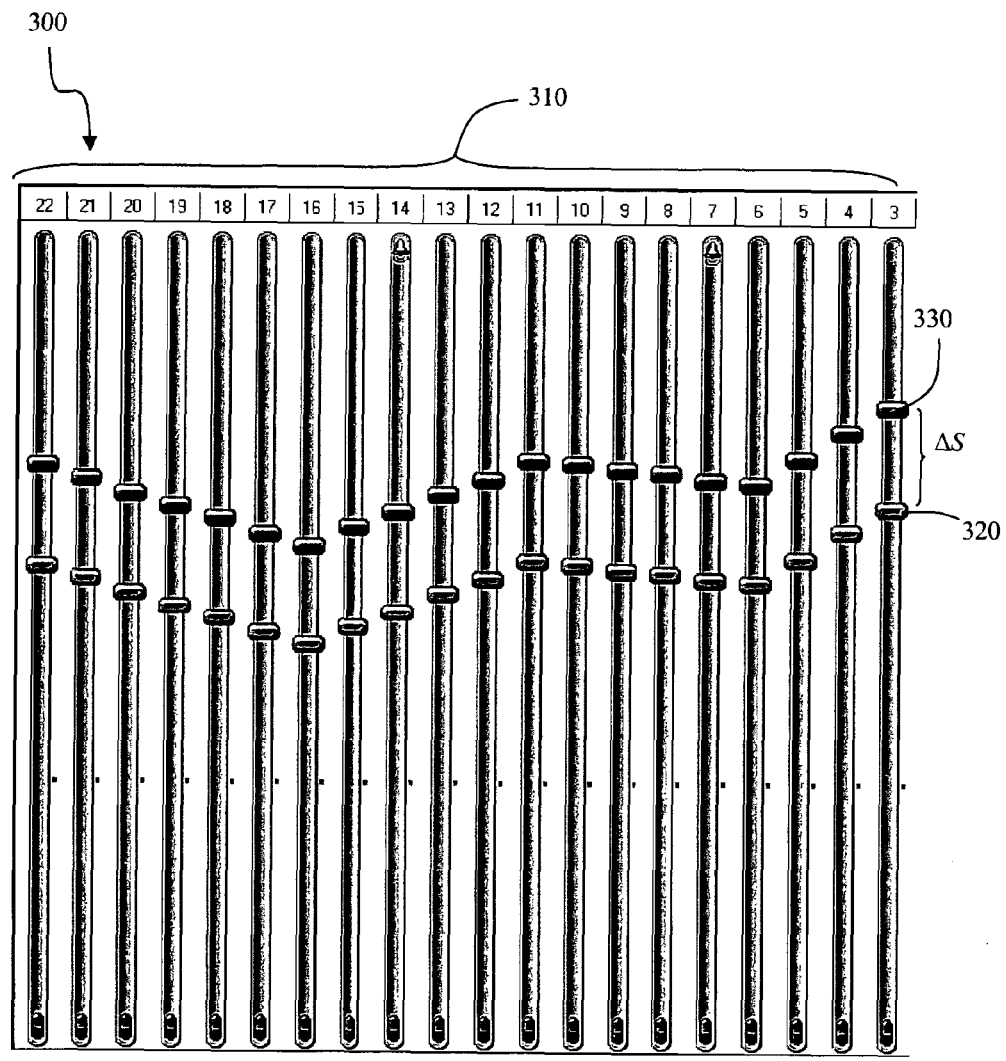
FIG. 3 is a graph of the T levels and C levels as function of the electrode number where the C level profile is a shifted version of the T level profile.
Figure 4:
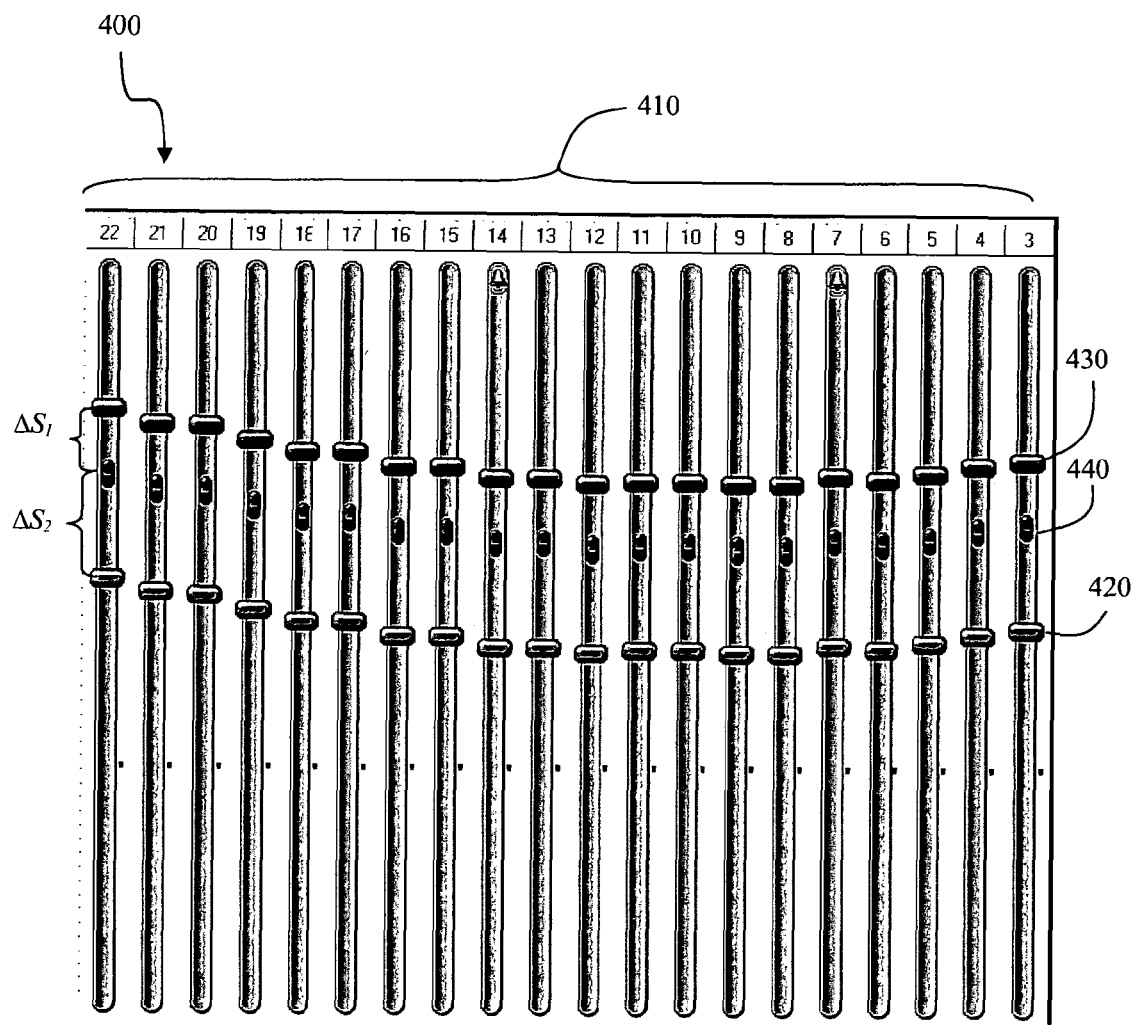
FIG. 4 is a graph of the T levels and C levels where the T level profile and the C level profile are shifted versions of an ECAP threshold profile.

Referring to FIG. 1, cochlear implant system 185 comprises external component assembly 100 and internal (or implanted) component assembly 124. External assembly 100 comprises a behind the ear (BTE) speech processing unit 126 connected to a transmission coil 130. The BTE unit includes a microphone 125 for detecting sound which is then processed by electronics within the BTE unit to generate coded signals. The coded signals are provided to an external transmitter unit 128, along with power from a power source such as a battery (not shown).

The internal component assembly 124 includes a receiver unit 132 having an internal coil (not shown) that receives and transmits power and coded signals from external assembly 100 to a stimulator unit 120 to apply the coded signal along an electrode assembly 140. Electrode assembly 140 enters cochlea 116 at cochleostomy region 122 and has one or more electrodes 142, positioned to be substantially aligned with portions of cochlea 116.

Cochlea 116 is tonotopically mapped with each region of the cochlea being responsive to acoustic and/or stimulus signals in a particular frequency range. To accommodate this property of cochlea 116, the cochlear implant system 185 includes an array 144 of electrodes each constructed and arranged to deliver suitable stimulating signals to particular regions of the cochlea, each representing a different frequency component of a received audio signal 107. Signals generated by stimulator unit 120 are applied by the electrodes 142 of electrode array 144 to cochlea 116, thereby stimulating the auditory nerve 150. It should be appreciated that although in FIG. 1 electrodes 142 are arranged in an array 144, other arrangements are possible.

Typically, the electrode array 144 includes a plurality of independent electrodes 142 each of which can be independently stimulated. As one of ordinary skill in the art is aware, low frequency sounds stimulate the basilar membrane most significantly at its apex, while higher frequencies more strongly stimulate the basilar membrane's base. Thus, electrodes 142 of electrode array 144 located near the base of the cochlea 116 are used to deliver high frequency stimulation signals while electrodes closer to the apex are used to deliver lower frequency stimulation signals.

Figure 5:
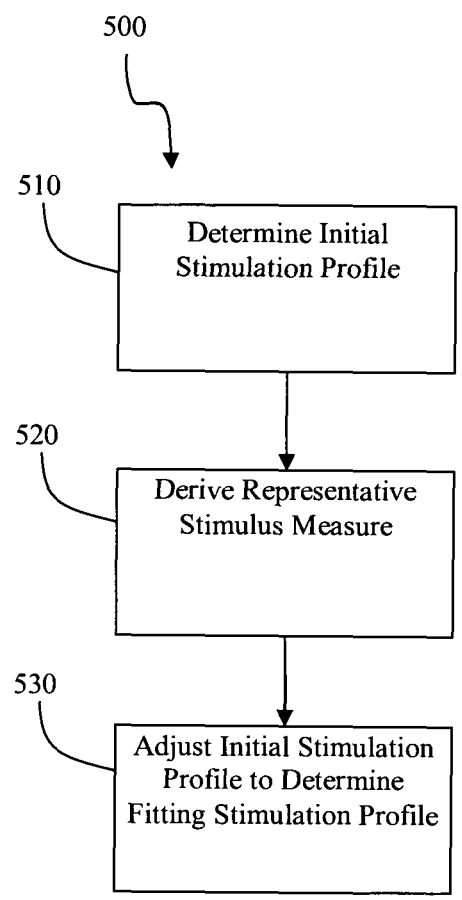
FIG. 5 is a flowchart of a method for fitting a medical implant according to a first illustrative embodiment of the present invention.

Referring now to FIG. 5, there is shown a flowchart 500 of a method for fitting a cochlear implant to a recipient in accordance with a first illustrative embodiment of the present invention.

At step 510, an initial stimulation profile is determined, hi one example, the initial stimulation profile may be measured objectively such as has been described previously or alternatively by clinical interaction with the recipient of the cochlear implant. In another alternative embodiment, the initial stimulation profile may be based in accordance with historical fitting data or be selected from a set of profiles based on the clinicians' fitting expertise.

At step 520, a representative stimulus level for the plurality of stimulation channels is derived from the initial stimulation profile. In this illustrative embodiment, the representative stimulus level relates to the mean stimulus level $\overline{L}$ which is calculated by summing the values of the initial stimulation profile over the stimulation channels and then dividing by the number of channels. This stimulus level accordingly reflects a representative stimulation level that is applied over the stimulation channels. In another embodiment, the representative stimulus level may be a single value chosen at a predetermined channel or alternatively be related to a selection of channels. In other embodiments, the representative simulation level may be the maximum, minimum or median value of the initial stimulation level.

At step 530, the fitting stimulation profile is determined based on the representative stimulus level which in this embodiment is the mean stimulus level $\overline{L}$ as described above. This representative stimulus level is then employed to modify or adjust the shape of the initial stimulation profile. In this embodiment, the initial stimulation profile is flattened or broadened in accordance with the mean stimulus level $\overline{L}$; that is, the mean stimulation level largely determines the degree to which the initial stimulation profile is modified.

Referring now to FIGS. 6A-6D, the adjustment of the initial stimulation profile involves the following steps:

1. subtracting the mean stimulus level $\overline{L}$ from each level along the initial stimulation profile 610 to provide a normalized stimulation profile 620 (see FIGS. 6 A and 6B);
2. multiplying each resulting level by a weighting factor W to provide an adjusted normalized stimulation profile 630 (a value of W<1 flattens the normalized stimulation profile 620, and a value of W>1 broadens the normalized stimulation profile 620) (see FIG. 6C); and
3. adding the mean stimulus level $\overline{L}$ to each level of the adjusted normalized stimulation profile 630 to result in fitting stimulation profile 640 (see FIG. 6D) that has been determined by modifying the shape of the initial stimulation profile 610.

The weighting factor depends primarily on the mean stimulus level $\overline{L}$ of the profile. In this embodiment, a simple linear function is used to derive the weighting factor. For example:

$$W=1.5-0.005\times \overline{L}_{INITIAL} \tag{1}$$

The mean stimulus level $\overline{L}$ is measured in current level (CL) units, which are normalized units ranging in this illustrative embodiment from 0 to 255. For the Freedom™ cochlear implant, the current (I) measured in µA is related to the CL by the following relationship:

$$I=17.5\times 100^{CL/255} \tag{2}$$

Figure 6A:
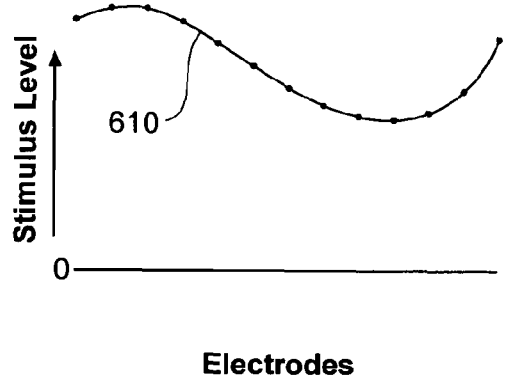
FIGS. 6A-6D depict graphically the various steps of a method for determining the fitting stimulation profile from the initial stimulation profile.
Figure 6B:
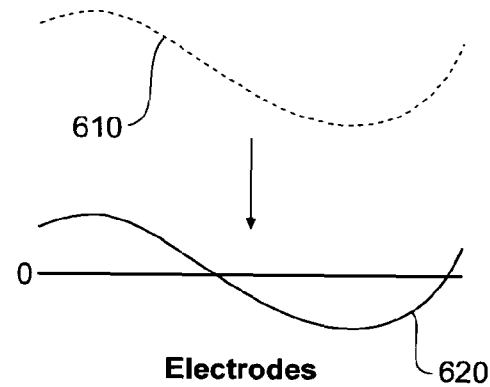
Figure 6C:
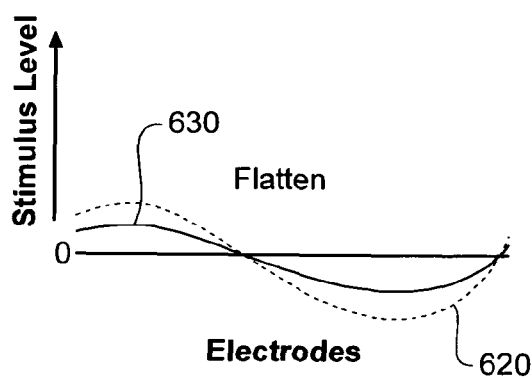
Figure 6D:
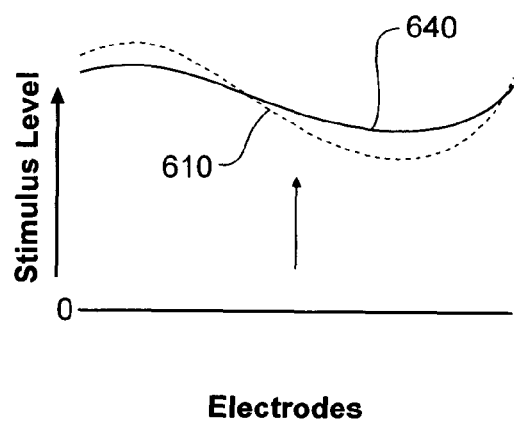

In this embodiment, a higher mean stimulus level leads to a smaller weighting thereby resulting in the initial stimulation profile 610 being flattened to determine the fitting stimulation profile 640 (see FIG. 6D).

Figure 7:
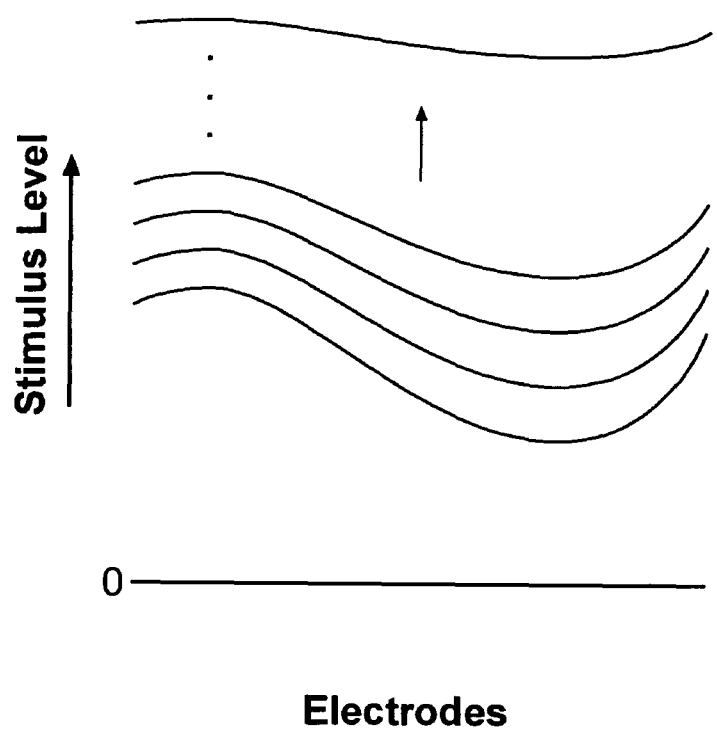
FIG. 7 depicts the effect on increasing stimulus level on the shape of the determined fitting stimulation profile in accordance with an illustrative embodiment of the present invention.

Referring now to FIG. 7, this process of adjustment can be seen with the fitting stimulation profile being flattened progressively as the mean stimulus level of the initial stimulation profile increases.

While in the previous embodiment the initial stimulation profile and the fitting stimulation profile have generally the same representative stimulus level, the present invention may be employed to determine a fitting stimulation profile having a different representative stimulus level than that of the initial stimulation profile. In this manner, data obtained with respect to the initial stimulation profile may be used as a basis to generate the fitting stimulation profile even though the fitting stimulation level is at a higher or lower overall stimulus level. Accordingly, in another embodiment a modified weighting factor W' is employed which takes into account the representative stimulus level such as the mean stimulus level of the initial stimulation profile rather than an absolute representative stimulus level of the final or fitting stimulation profile.

In this embodiment, W' is defined by the expression:

$$W'=1.0-0.0125\times (\overline{L}_{Fitting}-\overline{L}_{Initial}) \tag{3}$$

Once again, the mean stimulus level of both the fitting stimulation profile $\overline{L}_{Fitting}$ and the initial stimulation profile $\overline{L}_{Initial}$ are measured in CL.

As can be deduced from Equation 3, if the mean stimulus level of the derived or fitting stimulation profile is greater than the mean stimulus level of the initial stimulation profile, a weighting factor of less than 1 is applied resulting in the fitting stimulation profile being flatter than the initial stimulation profile. If $\overline{L}_{Fitting}$ is the same as that of the initial profile, a weighting factor of 1 is applied resulting in the stimulation profile and the initial stimulation profile being the same.

The adjustment or modification method described in these embodiments functions generally to progressively flatten the stimulation profile with an increase in the mean stimulus level $\overline{L}$ of the fitting stimulation profile with respect to the initial stimulation profile. This process of flattening takes into account the expected acceleration in loudness growth in the auditory system with increasing mean stimulus level and as such an initial stimulation profile may be readily adjusted based only on the mean stimulus level of the fitting stimulation profile.

The weighting factors W and W' specified by Equations 1 and 3 may be made recipient-specific which will take into account that loudness growth may differ across recipients, thereby adapting the weighting function to a given recipient's auditory system. In one embodiment, loudness growth may be psychophysical measured for each recipient (or even for each stimulation channel) and the results of these measurements may be employed to modify Equations 1 and 3. Furthermore, measurements of other objective physical characteristics may be used to predict a loudness growth function. For example, PCT Application No. PCT/AU2007/001369 entitled "MEDICAL IMPLANT CONFIGURATION METHOD", filed on 14 Sep. 2007, published 20 Mar. 2008, describes a machine learning system that may be employed to determine loudness growth and hence provide a recipient specific weighting function.

Figure 8:
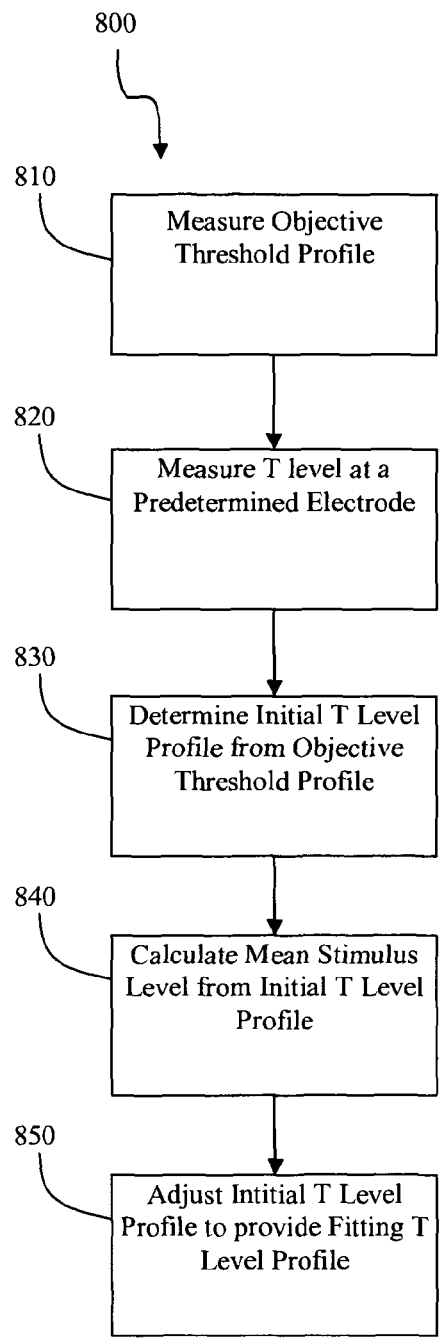
FIG. 8 is a flowchart of a method for clinically fitting a cochlear implant according to a second illustrative embodiment of the present invention.

In further illustrative embodiments, there are provided methods for clinically fitting a cochlear implant in accordance with the present invention. Referring now to FIG. 8, there is shown a flowchart of a clinical fitting method 800 for providing a fitting T level profile based on an initial objective threshold profile.

At step 810, a clinician obtains an initial stimulation profile by measuring an objective threshold profile via an appropriate objective measurement system as has been described previously. The thresholds can be ECAP, EABR, ESR thresholds, etc. ECAP thresholds can be obtained automatically via AutoNRT™ with the Nucleus® Freedom™ system, and AutoNRT™ could be incorporated into this exemplary clinical system.

At step 820, the clinician measures a single T level at a mid-array electrode by having the recipient indicate the minimum stimulus level that is repeatedly audible thereby determining an offset stimulus level for the T level profile.

At step 830, the T levels on all other electrodes are determined by shifting the objective threshold profile to form a shifted stimulation profile which passes through the single measured T or offset stimulus level of the previous step.

At step 840, the mean stimulus level $\overline{L}$ of the shifted stimulation profile is determined; and A step 850, the fitting T level profile is then determined by adjusting the shape of the initial stimulation profile according to Equation 1 or 3.

Figure 9:
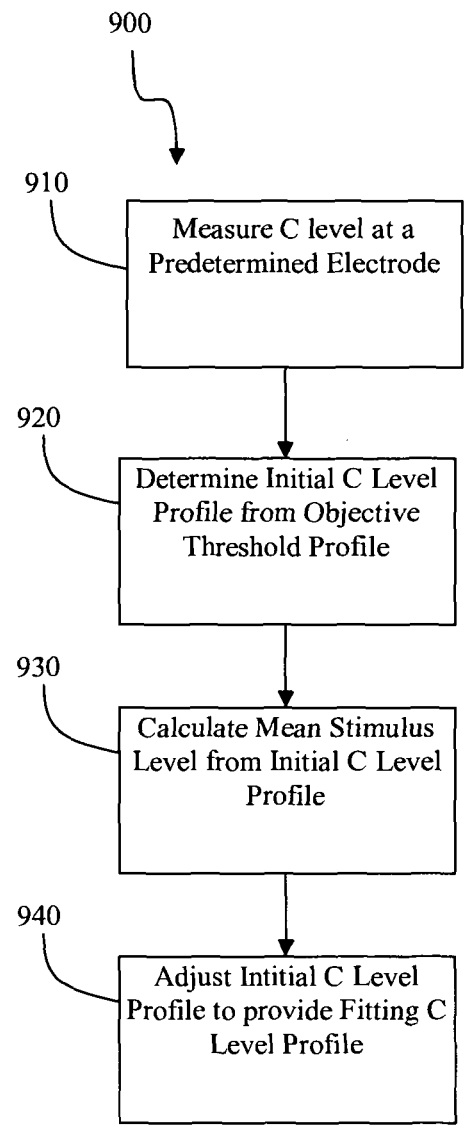
FIG. 9 is a flowchart of a method for clinically fitting a cochlear implant according to a third illustrative embodiment of the present invention.

Referring now to FIG. 9, there is shown a flowchart of a clinical fitting method 900 for providing a fitting C level profile based on an initial objective threshold profile.

At step 910, the clinician measures a single C level at the same mid-array electrode as referred to in step 820 by determining the maximum stimulus level that is not uncomfortable for the recipient thereby determining an offset stimulus level for the C level profile.

At step 920, the C levels on all other electrodes are determined by shifting the initial stimulation profile to form an initial stimulation profile which passes through the single measured C level of the previous step.

At step 930, the mean stimulus level $\overline{L}$ of the shifted stimulation profile is determined; and A step 940 the fitting C level profile is then determined by adjusting the shape of the initial stimulation threshold profile according to Equation 1 or 3.

Figure 10:
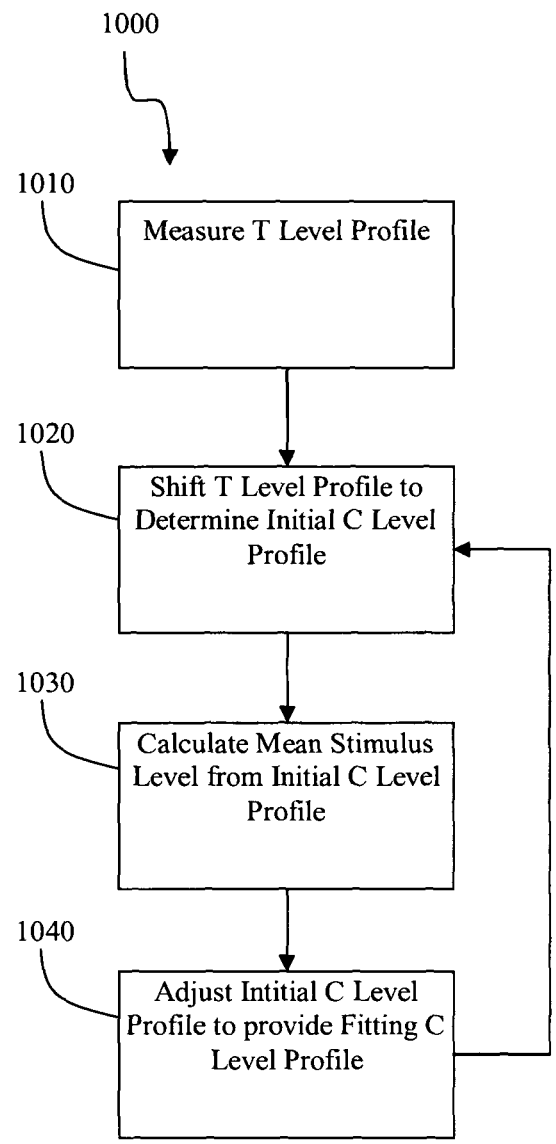
FIG. 10 is a flowchart of a method for clinically fitting a cochlear implant according to a fourth illustrative embodiment of the present invention.

Referring now to FIG. 10 there is shown a flowchart of a clinical fitting method 1000 for providing a fitting C level profile based on an initial clinically measured T level profile.

At step 1010, the clinician measures T levels at a number of channels along the electrode array creating a T level profile.

At step 1020, the clinician shifts the T level profile to higher stimulus levels in the presence of live sound to provide an initial C level profile.

At steps 1030 and 1040, the mean stimulus level $\overline{L}$ of the initial C level profile is determined and the initial C level profile is adjusted in accordance with Equation 3 to provide the fitting C level profile and the recipient then provides feedback as to their comfort level with the fitting C level profile. If based on this feedback, the initial C level profile is modified then the mean stimulus level is once again dynamically calculated for this new initial C level profile, which is adjusted again to provide the new fitting C level profile.

In another illustrative embodiment, the C level profile is clinically measured and then shifted to lower stimulus levels in the present of live sound to provide an initial T level profile. Similarly, the mean stimulus level $\overline{L}$ of the initial T level profile is determined and the initial T level profile is adjusted in accordance with Equation 3 to provide the fitting T level profile and the recipient then provides feedback as to whether they are able to detect sound with the fitting T level profile. If based on this feedback, the initial T level profile is modified then the mean stimulus level is once again dynamically calculated for this new initial T level profile, which is adjusted again to provide the new fitting T level profile.

Whilst in these illustrative embodiments, the C level profile is related to the maximum comfort level of electrical stimulation for the recipient, equally the C level profile could relate to an intermediate comfort level. As would be apparent to those skilled in the art, the present invention may also be extended to any number of stimulation profiles that may be required to parameterize and fit an implant. As an example, a cochlear implant may require the determination of three fitting stimulation profiles, i.e. a threshold level profile, an intermediate comfort level profile and a maximum comfort level profile. These profiles may then be determined in accordance with the present invention based on an initial stimulation profile which may be clinically measured (e.g. either any one of the threshold, intermediate comfort or maximum comfort level profiles) or objectively determined (e.g. the objective threshold profile).

The clinical fitting methods as described above would typically be implemented in a software system already used in the clinical fitting process involving the objective or clinical measurement of initial stimulation profiles as an additional module or processing means that would function to automatically replicate a given input profile such as the representative stimulation level, calculate characterization measures of an input profile and modify an input profile in accordance with predetermined relations such as Equations 1 and 3.

In another illustrative embodiment, the T and/or C level profiles may be adjusted in accordance with the present invention depending on the volume level chosen by the recipient thereby adjusting the performance of the medical implant. As the recipient increases or decreases the sound processor's volume setting, one or more of the operating stimulation profiles of the implant (i.e. the T and C level profiles) can be flattened or broadened respectively in accordance with the perceived stimulus level of the recipient's environment.

A brief consideration of the above described embodiments indicates that the invention improves the ability to quickly generate T and/or C level profiles based on an initial stimulation profile that has been measured either in a psychophysical^ or physiological manner that takes into account characteristics of the auditory system such as the effect of loudness perception in a recipient. As would be apparent to those skilled in the art, the accuracy improvement provided by the adjusted fitting stimulation profile is applied automatically by the cochlear implant and does not detract from the system's usability in any way.

Those of skill in the art would further appreciate that the steps of a method or algorithm described in connection with the illustrative embodiments disclosed herein may be embodied directly in hardware, in a software module executed by a processor, or in a combination of the two. To clearly illustrate this interchangeability of hardware and software, various illustrative components, blocks, modules and steps have been described above generally in terms of their functionality. Whether such functionality is implemented as hardware or software depends upon the particular application and design constraints imposed on the overall system.

Although illustrative embodiments of the present invention have been described in the foregoing detailed description, it will be understood that the invention is not limited to the embodiments disclosed, but is capable of numerous rearrangements, modifications and substitutions without departing from the scope of the invention as set forth and defined by the following claims.

The invention claimed is:

1. A computer-implemented method for fitting a medical implant to a recipient, the medical implant being operative to stimulate a physiological system of the recipient over a plurality of stimulation channels, the method comprising:
   determining, based on measurements of the physiological system of the recipient, an initial stimulation profile for the plurality of stimulation channels;
   determining one of a mean stimulus level of the initial stimulation profile and a median value of the initial stimulation profile;
   determining a fitting stimulation profile by modifying a shape of the initial stimulation profile based on the one of a mean stimulus level of the initial stimulation profile and a median value of the initial stimulation profile; and
   configuring the medical implant according to the fitting stimulation profile.

2. The computer-implemented method of claim 1, wherein the mean stimulus level of the initial stimulation profile is determined.

3. The computer-implemented method of claim 1, wherein the initial stimulation profile is an objectively measured profile and the fitting stimulation profile is a threshold level profile of the physiological system.

4. The computer-implemented method of claim 1, wherein the initial stimulation profile is an objectively measured profile and the fitting stimulation profile is a comfort level profile of the physiological system.

5. The computer-implemented method of claim 1, wherein the initial stimulation profile is a clinically measured threshold level profile of the physiological system and the fitting stimulation profile is a comfort level profile of the physiological system.

6. The computer-implemented method of claim 1, wherein the initial stimulation profile is a clinically measured comfort level profile of the physiological system and the fitting stimulation profile is a threshold level profile of the physiological system.

7. The computer-implemented method of claim 1, wherein modifying the shape of the initial stimulation profile comprises:
   multiplying the initial stimulation profile by a factor derived from the mean stimulus level of the initial stimulation profile.

8. The computer-implemented method of claim 1, wherein modifying the shape of the initial stimulation profile comprises:
   multiplying the initial stimulation profile by a factor that will produce a fitting stimulation profile for which a mean stimulus level is different than the mean stimulus level of the initial stimulation profile.

9. The computer-implemented method of claim 1, wherein modifying the shape of the initial stimulation profile includes flattening the initial stimulation profile to produce a mean stimulus level of the fitting stimulation profile that is greater than the mean stimulus level of the initial stimulation profile.

10. The computer-implemented method of claim 1, wherein the mean stimulus level of the initial stimulation profile is approximately the same as a mean stimulus level of the fitting stimulation profile.

11. A computer-implemented method for fitting a medical implant to a recipient, the medical implant being operative to stimulate a physiological system of the recipient over a plurality of stimulation channels, the method comprising:
   determining, based on measurements of the physiological system of the recipient, an initial stimulation profile for the plurality of stimulation channels; and
   determining a fitting stimulation profile by modifying a shape of the initial stimulation profile;
   wherein modifying the shape of the initial stimulation profile comprises:
      determining an offset stimulus level for the fitting stimulation profile;
      shifting the initial stimulation profile by the offset stimulus level to form a shifted stimulation profile;
      determining a representative stimulus level of the shifted stimulation profile;
      forming a normalized stimulation profile by subtracting the representative stimulus value from each of the values of the shifted stimulation profile;
      applying a weighting factor to each of the values of the normalized stimulation profile; and
      adding the representative stimulus level to each of the values of the weighted normalized stimulation profile to provide the fitting stimulation profile.

12. A computer-implemented method for fitting a stimulating hearing prosthesis operative to stimulate a portion of an auditory system of a recipient over a plurality of stimulation channels comprising:
   determining, based on measurements of a physiological system of the recipient, an initial stimulation profile for the plurality of stimulation channels; and
   determining a fitting stimulation profile by shifting the initial stimulation profile to a desired stimulation level, and flattening or broadening a shape of the initial stimulation profile based on whether a mean stimulus level of the fitting stimulation profile is greater or lesser than a mean stimulus level of the initial stimulation profile; and
   configuring the stimulating hearing prosthesis according to the fitting stimulation profile.

13. The computer-implemented method of claim 12, wherein the initial stimulation profile is a clinically measured threshold level profile of the physiological system and the fitting stimulation profile is a comfort level profile of the physiological system.

14. The computer-implemented method of claim 12, wherein the initial stimulation profile is a clinically measured comfort level profile of the physiological system and the fitting stimulation profile is a threshold level profile of the physiological system.

* * * * *